US010017735B2

(12) United States Patent
Tan et al.

(10) Patent No.: US 10,017,735 B2
(45) Date of Patent: Jul. 10, 2018

(54) CELL CULTURE OF CORNEAL ENDOTHELIAL CELLS

(71) Applicant: SINGAPORE HEALTH SERVICES PTE LTD, Singapore (SG)

(72) Inventors: Donald Tan, Singapore (SG); Jodhbir Mehta, Singapore (SG); Swee Lim Gary Peh, Singapore (SG)

(73) Assignee: SINGAPORE HEALTH SERVICES PTE LTD, Singapore (SG)

( * ) Notice: Subject to any disclaimer, the term of this patent is extended or adjusted under 35 U.S.C. 154(b) by 260 days.

(21) Appl. No.: 14/415,972

(22) PCT Filed: Jul. 18, 2013

(86) PCT No.: PCT/SG2013/000298
§ 371 (c)(1),
(2) Date: Jan. 20, 2015

(87) PCT Pub. No.: WO2014/014419
PCT Pub. Date: Jan. 23, 2014

(65) Prior Publication Data
US 2015/0203815 A1 Jul. 23, 2015

(30) Foreign Application Priority Data

Jul. 18, 2012 (SG) ................. 201205413-6

(51) Int. Cl.
*C12N 5/00* (2006.01)
*C12N 5/079* (2010.01)

(52) U.S. Cl.
CPC ........ *C12N 5/0621* (2013.01); *C12N 2500/24* (2013.01); *C12N 2500/25* (2013.01); *C12N 2500/30* (2013.01); *C12N 2500/32* (2013.01); *C12N 2500/34* (2013.01); *C12N 2500/38* (2013.01); *C12N 2500/62* (2013.01); *C12N 2500/72* (2013.01); *C12N 2500/80* (2013.01); *C12N 2501/06* (2013.01); *C12N 2501/10* (2013.01); *C12N 2501/31* (2013.01); *C12N 2501/33* (2013.01); *C12N 2501/39* (2013.01)

(58) Field of Classification Search
CPC .................................................. C12N 5/0621
See application file for complete search history.

(56) References Cited

U.S. PATENT DOCUMENTS

| 4,959,319 A | 9/1990 | Skelnik | |
|---|---|---|---|
| 2007/0275365 A1* | 11/2007 | Lui | A61L 27/3808 435/1.3 |
| 2011/0077270 A1* | 3/2011 | Pfeffer | A61K 31/00 514/313 |

FOREIGN PATENT DOCUMENTS

WO 2008103191 A1 8/2008

OTHER PUBLICATIONS

Bednarz et al., Br J Opthalmol 2001; 85; 1416-1420.*
International Preliminary Report on Patentability and Written Opinion of the International Searching Authority for Application No. PCT/SG2013/000298, dated Jan. 20, 2015 (7 pages).
International Search Report for International Application No. PCT/SG2013/000298, dated Sep. 17, 2013 (3 pages).
Bednarz, J. et al. "Effect of three different media on serum free culture of donor corneas and isolated human corneal endothelial cells" British Journal of Ophthalmology 2001, vol. 85, pp. 1416-1420.
Peh, G.S.L. et al. "Comparison of Five Culture Media for the Isolation and Propagation of Human Corneal Endothelial Cells" 2011 Annual Meeting of the Association for Research in Vision and Ophthalmology: ARVO 2011 Visionary Genomics, May 1-5, 2011, Fort Lauderdale, Flordia, USA, Program#/Poster# 6595; Methods, Results and Conclusions.
Peh, G.S.L. et al. 'Cultivation of Human Corneal Endothelial Cells Isolated from Paired Donor Corneas' PLoSONE 2011, vol. 6, e28310.
Peh, G.S.L. et al. 'Optimization of human corneal endothelial cell culture: density dependency of successful cultures in vitro' BMC Research Notes 2013, 6:176 whole of document.
Sølvik, U.Ø. et al. "Human serum-induced expression of e-selectin on porcine aortic endothelial cells in vitro is totally complement mediated" Transplantation 2001, vol. 72, pp. 1967-1973.
Peh et al., "Human Corneal Endothelial Cell Expansion for Corneal Endothelium Transplantation: An Overview" Transplantation 2011;91: 811-819.
Supplementary European Search Report corresponding to European Patent Application No. 13820042, dated Nov. 20, 2015.
Amano (2003) "Transplantation of Cultured Human Corneal Endothelial Cells" Cornea 22(Suppl 1):S66-S74.
Blake et al., (1997) "Matrix Stimulates the Proliferation of Human Corneal Endothelial Cells in Culture" Investigative Ophthalmology & Visual Science 38:6:1119-1129.
Engelmann and Friedl (1989) "Optimization of Culture Conditions for Human Corneal Endothelial Cells" In Vitro Cellular & Developmental Biology 25:11:1065-1072.
Engelmann and Friedl (1995) "Growth of Human corneal Endothelial cells in a Serum-reduced Medium" Cornea 14:1:62-70.
Ishino et al., (2004) "Amniotic Membrane as a Carrier for Cultivated Human Corneal Endothelial Cell Transplantation" Invest Ophthalmol Vis Sci. 45:800-806.
Lee and Kay (2012) "NF-κB Is the Transcription Factor for FGF-2 That Causes Endothelial Mesenchymal Transformation in Cornea" Invest Ophthalmol Vis Sci 53:1530-1538.

(Continued)

*Primary Examiner* — Ruth A Davis
(74) *Attorney, Agent, or Firm* — Lathrop Gage LLP; Brian C. Trinque (57) ABSTRACT

The invention relates to a dual-media approach for culturing isolated corneal endothelial cells. Isolated corneal endothelial cells are first contacted with a proliferative medium to propagate and/or expand the endothelial cells followed by a maintenance medium to preserve the morphology and/or characteristics of the corneal endothelial cells. The invention includes the proliferative medium and the maintenance medium and also a combination of the two medium.

15 Claims, 9 Drawing Sheets

(56) References Cited

OTHER PUBLICATIONS

Li et al., (2007) "A Novel Method of Isolation, Preservation, and Expansion of Human Corneal Endothelial Cells" Invest Ophthalmol Vis Sci. 48(2):614-620.

Miyata et al., (2001) "Effect of Donor Age on Morphologic Variation of Cultured Human Corneal Endothelial Cells" Cornea 20(1):59-63.

Yu et al., (1988) "Human Corneal Endothelial Cells: Isolation, Characterization and Long-term Cultivation" Exp. Eye Res. 47:403-414.

Yue et al., (1989) "Growth of Human Corneal Endothelial Cells in Culture" Investigative Ophthalmology & Visual Science, 30:2:248-253.

Zhu and Joyce (2004) "Proliferative Response of Corneal Endothelial Cells from Young and Older Donors" Invest Ophthalmol Vis Sci. 45:1743-1751.

* cited by examiner

CELL CULTURE OF CORNEAL ENDOTHELIAL CELLS

RELATED APPLICATIONS

This application is a 35 U.S.C. § 371 filing of International Application No. PCT/SG2013/000298, filed Jul. 18, 2013, which claims priority to Singapore Patent Application No. 201205413-6, filed Jul. 18, 2012, each of which is incorporated herein by reference in its entirety.

FIELD OF THE INVENTION

The present invention relates to the field of cell culture. In particular, the present invention relates to culture of corneal endothelial cells.

BACKGROUND OF THE INVENTION

The human corneal endothelium forms an essential layer of the cornea, maintaining corneal transparency through the regulation of corneal hydration. The endothelial cell layer does not actively regenerate in vivo. Hence, there remains a need for corneal allograft transplantation in cases of accelerated endothelial cell loss due to genetic disease, generic eye infection, or more acute cell loss caused by accidental and surgical trauma or previous corneal surgery. Although current corneal transplantation is successful in the short term, there is a risk of graft rejection, and long-term graft failure is a problem. Moreover, global shortage of cornea donors greatly restricts the number of corneal transplantation performed.

It is now possible to isolate and culture human corneal endothelial cells (HCECs) in vitro, thus providing new opportunity for in-depth cell biological studies and development of potential tissue-engineered human corneal endothelium graft alternative. In order to generate the required numbers of HCECs for further biological studies and future development of tissue-engineered human corneal endothelium, isolated primary HCECs must be propagated for at least three rounds of passages to achieve a sizeable amount of cells for experimental research. However, on repeated passages, the human corneal endothelial cells may develop into fibroblastic-like cells.

It is therefore desirable to develop effective techniques (for example either a novel approach or a single culture medium) to support the propagation of isolated HCECs, as well as to maintain their characteristic morphology.

SUMMARY OF THE INVENTION

According to a first aspect, the present invention relates to a method for culturing isolated corneal endothelial cells comprising the steps of:
(i) contacting isolated corneal endothelial cells with a proliferative medium to propagate and/or expand corneal endothelial cells; and
(ii) contacting the propagated and/or expanded corneal endothelial cells with a maintenance medium to substantially preserve the morphology and characteristics of the corneal endothelial cells.

The present invention also relates to a combination comprising a proliferative medium comprising a supplemented basal medium to propagate and/or expand corneal endothelial cells; and a maintenance medium comprising a basal medium to substantially preserve the morphology and characteristics of corneal endothelial cells.

The invention further relates to a maintenance medium for substantially preserving the morphology and/or characteristic of an isolated population of corneal endothelial cells subsequent to expansion and/or propagation of the corneal endothelial cells with a proliferative medium.

The corneal endothelial cells may be derived from any animal source. For example, the corneal endothelial cells could be from a mammal. Examples of suitable sources include but are not limited to, bovine, equine porcine or primate (for example: human, simian). In particular, the corneal endothelial cells may be from a human.

The invention also relates to an isolated population of corneal endothelial cells. The isolated population of corneal endothelial cells may comprise at least one cell. In particular, the invention relates to an isolated population of corneal endothelial cells prepared/preparable by a method according to any aspect of the invention.

BRIEF DESCRIPTION OF THE FIGURES

FIG. 1. (A) Coronet vacuum suction cup (or vacuum donor punch) with a research cornea held in place (insert); (B) Peeled Descemet's Membrane and corneal endothelium (DM-CE) layer (200 µm); (C) DM-CE layer showing the unique morphology of corneal endothelial cells (50 µm); (D) Collagenased DM-CE layer ~2 hours (100 µm); (E) Tightly compacted Corneal Endothelial (CE) clusters after collagenase treatment >2 hours (100 µm); (F) Clusters of CE after further dissociation using TryPLE Express for approximately 5 minutes (100 µm); (G) Attachment and morphology of Human Corneal Endothelial Cells (HCECs) without FNC coating (6 hrs|42 hrs); (H) Attachment and morphology of HCECs with FNC coating (6 hrs|42 hrs); (I) Graph—attachment with and without FNC coating as analyzed by xCELLigence real-time impedance-based cell analyzer system (Roche).

FIG. 6. Schematic diagram depicting the propagation of human CECs using a dual media approach. A: Procurement—pairs of research-grade corneas used in this study were procured from Lions Eye Institute for Transplant and Research Inc. (Tampa, Fla.). Research corneas were preserved and transported in Optisol-GS, and processed within 14 days from preservation. B: Process and isolation—once received, corneas were processed within 1 day where the CECs were isolated and plated as passage 0 culture. C to C': Stabilization—isolated human CECs were seeded and allowed to attach and stabilize in M5 medium overnight. C' to C'': Proliferation—to promote the proliferation of the adhered CECs, M4 medium was utilized throughout the expansion phase. C'' to D: Stabilization and maintenance—when expanding human CECs became approximately 80% confluent, M5 medium was re-introduced for at least seven days, which aided in the preservation of the cellular morphology of cultivated human CECs. Thereafter, confluent human CECs were dissociated using TE, seeded at a density of $1\times10^4$ cells per $cm^2$, and subjected to the same inter-switching dual-mediamedium approach for subsequent passages.

FIG. 7(A): Single media propagation of HCECs; After the isolation (A.I) of primary HCECs, the isolated HCECs were expanded from (A.II) P0 to (A.III) P1 using one culture medium. In the dual media approach (B): Dual media propagation of HCECs; After processing (B.I), the isolated HCECs were left to attach in M5 (II) for around 24 hours. On the following day, the adhered HCECs were switched into a more proliferative culture medium, usually M2 or M4 for another 7 to 14 days or until the primary HCECs became 80% confluent. Once 80% confluency was attained, the culture medium was reverted back into M5 for at least 7 day before (III) passaging into the next passage.

DEFINITIONS

Basal medium refers to a medium comprising a carbon source and salts for cell culture.

Cell culture refers to the maintenance or growth of isolated cells in vitro, typically in an artificial environment. Cell culture includes cell expansion or propagation.

Cell expansion refers to cell culture where there is an increase in the number of cells. Cell expansion and cell propagation may be used interchangeably.

Cell passage refers to the splitting (dilution) and subsequent redistribution of a monolayer or cell suspension into culture vessels containing fresh medium. This is performed when the cells reached a desired level of density (for example ~90%-100% confluency).

The term passage number refers to the number of times that a cell population has been removed from the culture vessel and undergone a passage process.

In cell culture biology, confluency is the term commonly used as a measure of the coverage of the dish or the flask by the cells. For example, 100 percent confluency means the dish is completely covered by the cells, and therefore no more room is left for the cells to grow; whereas 50 percent confluency means roughly half of the dish is covered and there is still room for cells to grow.

DETAILED DESCRIPTION OF THE INVENTION

The present invention generally relates to a dual medium method for culturing isolated corneal endothelial cells.

Accordingly, the present invention relates to a method for culturing isolated corneal endothelial cells comprising the steps of:
(i) contacting isolated corneal endothelial cells with a proliferative medium to propagate and/or expand corneal endothelial cells; and
(ii) contacting the propagated and/or expanded corneal endothelial cells with a maintenance medium to substantially preserve the morphology and characteristics of the corneal endothelial cells.

With the dual medium method, the isolated corneal endothelial cells are cultured in the proliferative medium for a suitable number of passages. The isolated corneal endothelial cells are allowed to propagate and/or expand in the proliferative medium. However, before further differentiation and/or changes in the morphology of the corneal endothelial cells occur, the isolated corneal endothelial cells are contacted with the maintenance medium. The morphology and characteristics of the corneal endothelial cells are substantially preserved in the maintenance medium.

For example, step (i) comprises culturing the isolated corneal endothelial cells in the proliferative medium.

Step (ii) is performed before the isolated corneal endothelial cells differentiate or change morphology and/or characteristics. In one example, step (ii) comprises replacing the proliferative medium with the maintenance medium. In particular, step (ii) comprises culturing the propagated and/or expanded corneal endothelial cells in the maintenance medium. Accordingly, step (ii) includes passaging the propagated and/or expanded corneal endothelial cells in the maintenance medium.

In addition, the invention also relates to a combination comprising a proliferative medium comprising a supplemented basal medium to propagate and/or expand corneal endothelial cells; and a maintenance medium comprising a basal medium to substantially preserve the morphology and characteristics of the corneal endothelial cells.

Further, the invention also relates to a composition comprising a maintenance medium for substantially preserving the morphology and/or characteristic of an isolated population of corneal endothelial cells subsequent to expansion and/or propagation of the corneal endothelial cells with a proliferative medium.

The proliferative media has a different formulation from the maintenance media. For example, the components of the proliferative media supports expansion and/or propagation of cells while the components of the basal media supports the viability of cells with little changes but does not support expansion and/or propagation of cells.

Any suitable proliferative medium may be applicable for any aspect of the invention. The proliferative medium is used for propagating and/or expanding the corneal endothelial cells. The proliferative medium may comprise a supplemented basal medium.

For example, the supplemented basal medium may be a commercial basal medium supplemented accordingly to support expansion and/or propagation of cells. Examples of supplemented basal media include but are not limited to supplemented Minimum Essential Medium (MEM); supplemented Dulbeco's Modified Eagles' Medium (DMEM), Opti-MEM-I, supplemented Supplemental Hormonal Epithelial Medium (SHEM), Medium 199 (M199) or F99 medium. Examples of supplemented basal media are listed in Tables 1 and 2.

In particular, the proliferative medium comprises a basal medium supplemented with serum. The proliferative medium may comprise a basal medium supplemented with any suitable amount of serum. For example, the proliferative medium may comprise a basal medium supplemented with at least 2% serum. Other examples of serum amount in the basal medium for the proliferative medium include 2% to 30%. Accordingly, the serum amount in the basal medium for the proliferative medium includes 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21.5%, 22%, 22.5%, 23%, 23.5%, 24%, 24.5%, 25%, 25.5%, 26%, 26.5%, 27%, 27.5%, 28%, 28.5%, 29%, 29.5% and 30%. In particular, the proliferative medium comprises a basal medium supplemented with 5% serum.

The proliferative medium may further comprise a basal medium supplemented with at least one supplement selected from the group consisting of amino acids, antimicrobials, cholera toxin, chondroitin, Dimethyl sulphoxide (DMSO), Endothelial Cell Growth Supplement (ECGS), growth factors, insulin, steroids, minerals, pituitary extract, transferrin and vitamins.

Any suitable maintenance medium may be used for substantially preserving the morphology and/or characteristic of the corneal endothelial cells. For example, the maintenance medium comprises a basal medium. In particular, the maintenance medium comprises a basal medium supplemented with serum. For example, the maintenance medium may comprise a basal medium supplemented with at least 2% serum. Other examples of serum amount in the basal medium for the maintenance medium include 2% to 30%. Accordingly, the serum amount in the basal medium for the maintenance medium includes 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21.5%, 22%, 22.5%, 23%, 23.5%, 24%, 24.5%, 25%, 25.5%, 26%, 26.5%, 27%, 27.5%, 28%, 28.5%, 29%, 29.5% and 30%. In particular, the maintenance medium comprises a basal medium supplemented with 2.5% or 5% serum.

The maintenance medium or basal medium may be a commercially available maintenance medium or basal medium. For example, the maintenance or basal medium comprises Human Endothelial-Serum Free Medium (Human Endothelial-SFM).

The maintenance medium may also be supplemented with at least one antimicrobial.

The serum for the proliferative media or the maintenance media may be from any suitable animal source. For example, the serum could be from a mammal. Examples of suitable animal sources include but are not limited to, bovine, equine porcine or primate (for example: human, simian). Additionally, the serum may be from a fetal source or an adult source.

The amino acids may comprise essential (for example glutamine or L-glutamine) and/or non-essential amino acids.

The antimicrobials may comprise antibiotics, antifungals and/or antimycotics. Examples of antimicrobials include but are not limited to amphotericin B, doxycycline, fungizone, gentamicin, penicillin, primocin or streptomycin.

Chondroitin may be in the form of chondroitin sulphate.

Examples of growth factors include but are not limited to basic fibroblast growth factor (bFGF), epidermal growth factor (EGF) or nerve growth factor (NGF).

The insulin may be derived from any suitable source, including but not limited to bovine, equine, porcine or primate (for example: human, simian). The insulin may also be recombinant insulin.

Examples of steroids include but are not limited to hydrocortisone.

Examples of minerals include but are not limited to calcium chloride, sodium chloride or sodium selenite.

Examples of vitamins include but are not limited to ascorbic acid.

EXAMPLES

Having now generally described the invention, the same will be more readily understood through reference to the following examples, which are provided by way of illustration, and are not intended to be limiting of the present invention.

Standard molecular biology techniques known in the art and not specifically described were generally followed as described in Green and Sambrook, Molecular Cloning: A Laboratory Manual, Cold Springs Harbor Laboratory, New York (2012).

Example 1 Isolation of Primary HCECs

Figure 1:
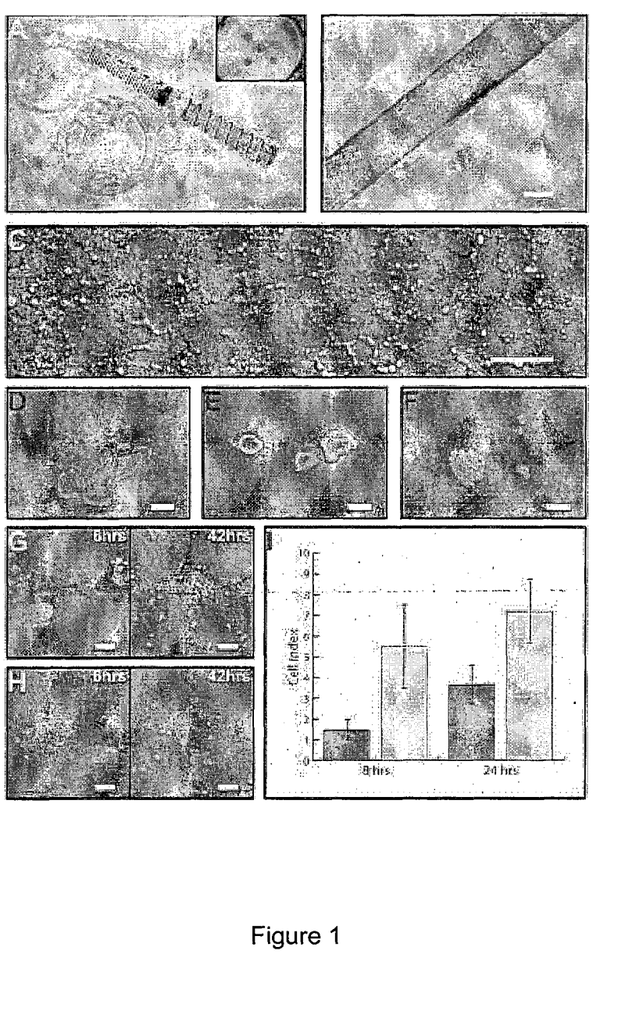

A working protocol for the isolation and establishment of primary HCECs was adapted for this study (FIG. 1). Isolation of primary HCECs involved a two-step, peel-and-digest method. Firstly, the thin corneal DM-endothelial layer was carefully peeled off under the dissecting microscope with the aid of a vacuum suction cup (or vacuum donor punch) to hold the cornea in place [FIG. 1(A)]. Much caution was taken in the peeling process to prevent the potential contamination of the posterior corneal stroma. Isolated DM-endothelial layer sheet [FIG. 1(B)] was subsequently subjected to an enzymatic digestion using collagenase (2 mg/mL) for at least 2 hours, and up to 4 hours to release the corneal endothelium from the DM [FIGS. 1(D) and (E)]. Length of collagenase treatment is variable and is believed to be donor dependent. Clusters of collagenase-treated HCECs can be dissociated further with a brief treatment of TrypLE Express [FIG. 1(F)]. Following a quick rinse in PBS+, isolated HCECs were plated onto FnC mixture coated tissue culture surfaces and expanded in the various medium for comparison (Table 2).

Example 2 Comparison of Culture Media

Figure 2:
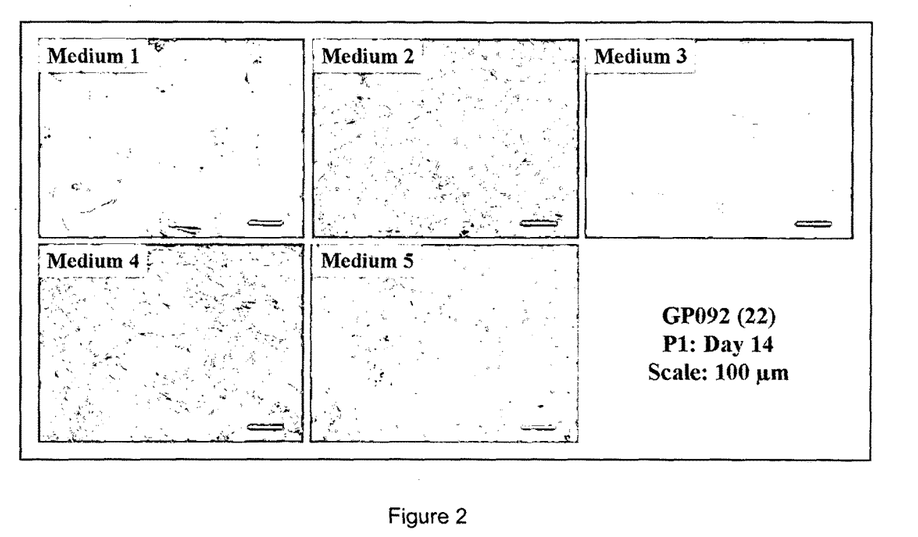
FIG. 2. Comparison of the morphology of HCECs grown in the 5 culture media. At P1, morphology of HCECs cultured in M2 and M4 appeared to be small and compact. HCECs cultured in M1 and M3 appeared to be retaining their polygonal morphology, but appeared to be larger in cell size. HCECs cultured in M5 appeared to retain morphology relatively comparable to the nave corneal endothelium (Scale bar ~100 µm).
Figure 3:
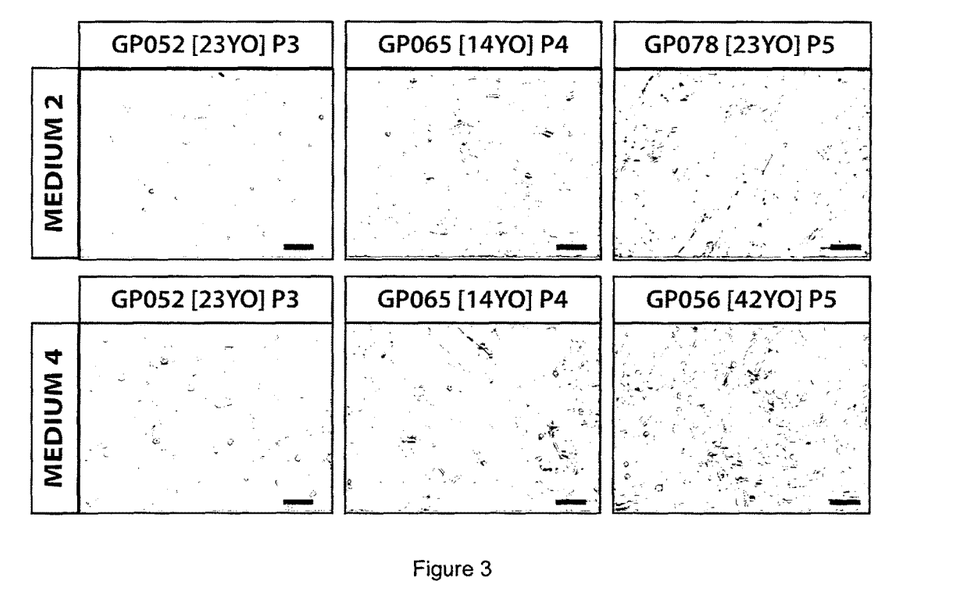
FIG. 3 HCECs cultured in M2 or M4 at P3, P4 and P5 showing heterogeneous fibroblastic cellular morphology (Scale bar ~100 µm).
Figure 4:
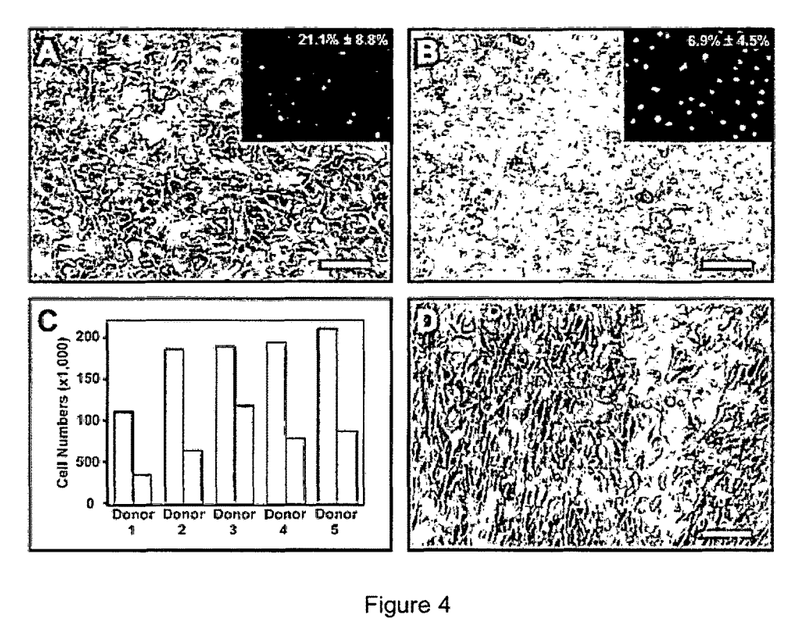
FIG. 4 Human Corneal Endothelial Cells (CECs) established and propagated in M4 only and in M5 only. Representative sets of photomicrographs showing morphology of confluent human CECs (P0) established in (A): M4 only; (insert) percentages of proliferative human CECs (at the first passage) as assessed by the Click-IT EdU assay; and in (B): M5 only; (insert) percentages of proliferative human CECs (at the first passage). (C): Bar graphs showing total cell numbers obtained for the passage of five independent sets of human CECs cultured in M4 only (green) compared to M5 only (blue). (D): Representative photomicrograph showing a typical fibroblast-like morphology of cultivated human CECs at the third passage cultured using M4 only.

There are various serum-supplemented culture media reported for the in vitro serum-supplemented culture media were compared (Table 2), each developed from a different basal medium coded here as M1-DMEM (10% serum); M2-OptiMEM-I (8% serum); M3-DMEM/F12 (5% serum), & M4-Ham's F12/M199 (5% serum). It was shown that cultured HCECs can be established in all four culture media [Passage 1 (P1), FIG. 2] but only M2 and M4 were able to promote and support their continual proliferation beyond the second passage. However, HCECs cultured in M2 and M4 became heterogeneous, usually by the third passage (sometimes as early as the second passage), taking up a more fibroblastic morphology [see later; FIG. 3]. In particular, although HCECs grown in M4 can be propagated beyond the second passage, the formation of fibroblastic-like cells became evident [FIG. 4(D)].

Figure 5:
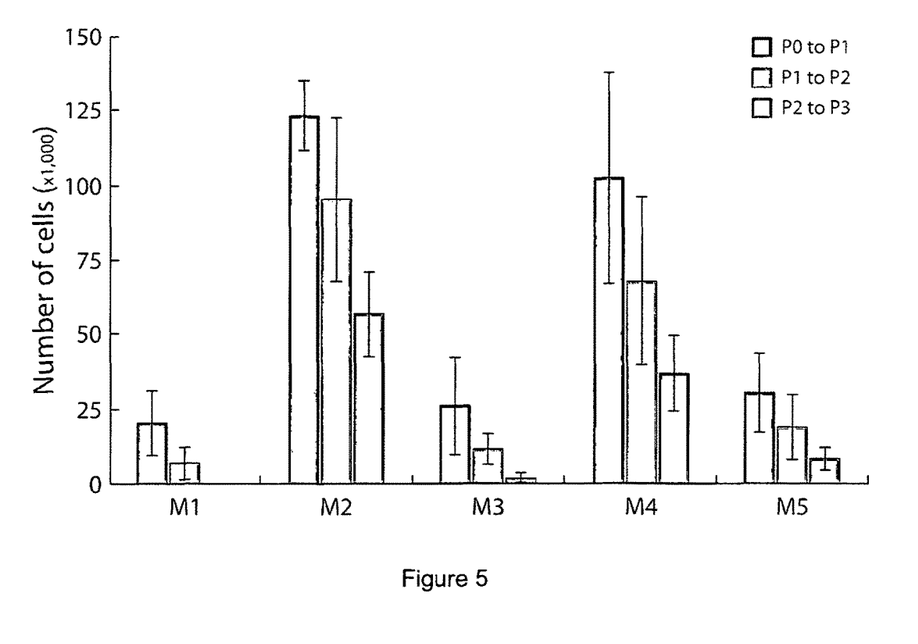
FIG. 5. Proliferative capacity of primary HCECs in the 5 culture media. HCECs cultured in M2 and M4 are the most proliferative. Neither M1 nor M3 was able to support the propagation of HCEC beyond P2. M5 was able to support some the proliferation of HCECs, predominately those established from younger donors.
Figure 6:
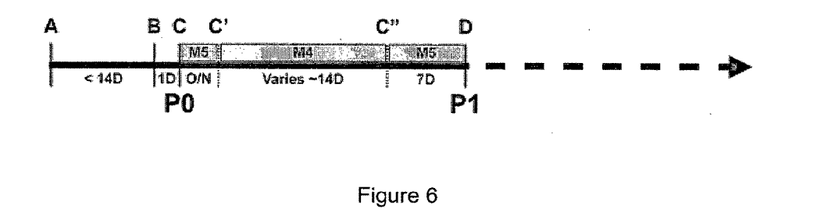

The inventors found that a maintenance medium could be used for the limited propagation of HCECs derived from donor corneas. For example, the inventors were the first to use a maintenance medium M5 consisting of a basal medium known as human Endothelial-Serum Free Medium (Human Endothelial-SFM; Gibco BRL) supplemented with 5% fetal bovine serum (FBS), This formulation allows the isolation and limited propagation of HCECs derived from donor corneas. More importantly, the unique morphology of HCECs established in M5 is preserved, and is far superior compared to the other four media M1-M4 [FIG. 2]. Although homogeneous culture of HCECs can be established in M5 without the formation of fibroblastic-like cells when compared to M2 or M4, the rate of proliferation as gauged by Click-IT EdU showed slower growth when compared to cultures grown in M4. Data obtained from 5 independent donors confirmed these results and limited numbers of HCECs can be obtained when using M5 alone (FIG. 5). However, due to the lower number of cells obtained when grown in M5 alone, HCECs could not be effectively passaged beyond the second round of passage.

In terms of the proliferative rate of HCECs cultured (for three passages) in M5, preliminary results showed that it is superior to M1 or M3, but is not as good as M2 or M4 (FIG. 5).

TABLE 1

Supplemented media used in the culture of human corneal endothelial cells

| Basal Medium | Serum* | Growth Factors/ Supplements | Reference |
|---|---|---|---|
| MEM | 10% | 5 µg/ml insulin<br>5 µg/ml transferrin<br>5 ng/ml sodium selenite<br>150 µg/ml ECGS<br>50 µg/ml gentamicin<br>100 U/ml penicillin<br>100 µg/ml streptomycin<br>0.25 µg/ml amphotericin B | Blake et al., 1997 |
| MEM | 15% | 200 mM glutamine<br>2% essential amino acids<br>1% non-essential amino acids<br>10 µg/ml gentamicin<br>1.2 µg/ml amphotericin B | Yue et al., 1989 |
| DMEM | 15% | 30 mg/L L-glutamine<br>2.5 mg/L Fungizone<br>2.5 mg/L doxycycline<br>2 ng/mL bFGF | Miyata et al., 2001<br>Amano 2003 |
| M199 | 20% | 4 mM glutamine<br>200 µg/ml ECGS<br>100 µg/ml penicillin<br>100 µg/ml streptomycin | Pistsov et al., 1988 |
| DMEM (M1) | 10% | 2 ng/ml bFGF<br>50 U/ml penicillin<br>50 µg/ml streptomycin | Ishino et al., 2004 |
| Opti-MEM-I (M2) | 8% | 20 ng/ml NGF<br>5 ng/ml EGF<br>20 µg/ml ascorbic acid<br>200 mg/L calcium chloride<br>100 µg/ml pituitary extract<br>50 µg/ml gentamicin<br>1 X antibiotic/antimycotic<br>0.08% chondroitin sulphate | Zhu and Joyce, 2004 |
| SHEM (M3)<br>Ham's F12 & DMEM<br>(1:1 ratio) | 5% | 0.5% DMSO<br>2 ng/ml EGF<br>5 µg/ml insulin<br>5 µg/ml transferrin<br>5 ng/ml ng/ml<br>0.5 µg/ml hydrocortisone<br>1 nM cholera toxin<br>50 µg/ml gentamicin<br>1.25 µg/ml amphotericin B | Li et al., 2007 |
| F99 (M4)<br>Ham's F12 & M199<br>(1:1 ratio) | 2%-5% | 20 µg/ml ascorbic acid<br>20 µg/ml bovine insulin<br>2.5 µg/ml transferrin<br>0.6 ng/ml sodium selenite<br>10 ng/ml bFGF | Engelmann and Friedl, 1989<br>Engelmann and Friedl, 1995 |

TABLE 2

Supplemented media used in the comparison culture of human corneal endothelial cells

| Basal Medium | Serum* | Growth Factors/ Supplements | Reference |
|---|---|---|---|
| DMEM (M1) | 10% | 2 ng/ml bFGF<br>50 U/ml penicillin<br>50 µg/ml streptomycin | Ishino et al., 2004 |
| Opti-MEM-1 (M2) | 8% | 20 ng/ml NGF<br>5 ng/ml EGF<br>20 µg/ml ascorbic acid<br>200 mg/L calcium chloride<br>100 µg/ml pituitary extract<br>50 µg/ml gentamicin<br>1 X antibiotic/antimycotic<br>0.08% chondroitin sulphate | Zhu and Joyce, 2004 |
| SHEM (M3)<br>Ham's F12 & DMEM<br>(1:1 ratio) | 5% | 0.5% DMSO<br>2 ng/ml EGF<br>5 µg/ml insulin<br>5 µg/ml transferrin<br>5 ng/ml ng/ml<br>0.5 µg/ml hydrocortisone<br>1 nM cholera toxin<br>50 µg/ml gentamicin<br>1.25 µg/ml amphotericin B | Li et al., 2007 |
| F99 (M4)<br>Ham's F12 & M199<br>(1:1 ratio) | 2%-5% | 20 µg/ml ascorbic acid<br>20 µg/ml bovine insulin<br>2.5 µg/ml transferrin<br>0.6 ng/ml sodium selenite<br>10 ng/ml bFGF | Engelmann and Friedl, 1989<br>Engelmann and Friedl, 1995 |
| Endothelial-SFM (M5) | 5% | 100 µg/ml primocin | SERI |

Example 3: Dual Media Culture

The use of a dual media culture was then investigated. Interestingly, exposure of HCECs cultured in the proliferative medium M2 or M4 to M5 improved the morphology of HCECs. Interestingly, when Endothelial-SFM was used with either 2.5% [Endo2.5%] or 5% [Endo5%] fetal bovine serum (FBS) as the respective maintenance medium, long-term (>30 days) maintenance of HCECs is possible with a regular medium change every 48 to 72 hours.

Exposure of HCECs expanded in the proliferative medium M4 to the maintenance medium M5 in 80%-90% confluent HCECs cultured were found to be beneficial to the cultivated cells and improvement to the morphology of the HCECs were observed. For example, the use of both M4 and M5 in the culture of HCECs as a dual media approach relies on the timely incorporation of M5 as depicted in the schematic diagram in FIG. 4. When placed in M5 after culturing in proliferative medium, long-term (>30 days) maintenance of HCECs is possible with a regular medium change every 48 to 72 hours.

It was found that the use of a dual media culture system for the expansion of HCECs is (1) to be able to obtain sizeable numbers in the expansion of isolated primary HCECs expanded over at least three passages using a medium that is able to support the proliferation of HCECs, and (2) to be able to prevent fibroblastic transformation of cultivated HCECs using a medium that has the capacity to maintain the classical hexagonal and/or polygonal cellular appearance of cultivated corneal endothelial cells, similar to cells of the nave corneal endothelium layer.

Accordingly, this invention encompasses the in vitro serial cultivation of primary HCECs using a novel two media approach. For example, medium A (proliferative medium—M4) is a medium that supports the proliferation of HCECs and medium B (maintenance medium—M5) is a medium that stabilizes and maintains the unique cellular morphology of the expanded HCECs for at least three rounds of passages. An alternative dual media approach using the dual media culture system in the expansion and maintenance of isolated primary HCECs is depicted in FIG. 7(B). For comparison, FIG. 7(A) shows an example of the single media approach.

Figure 8:
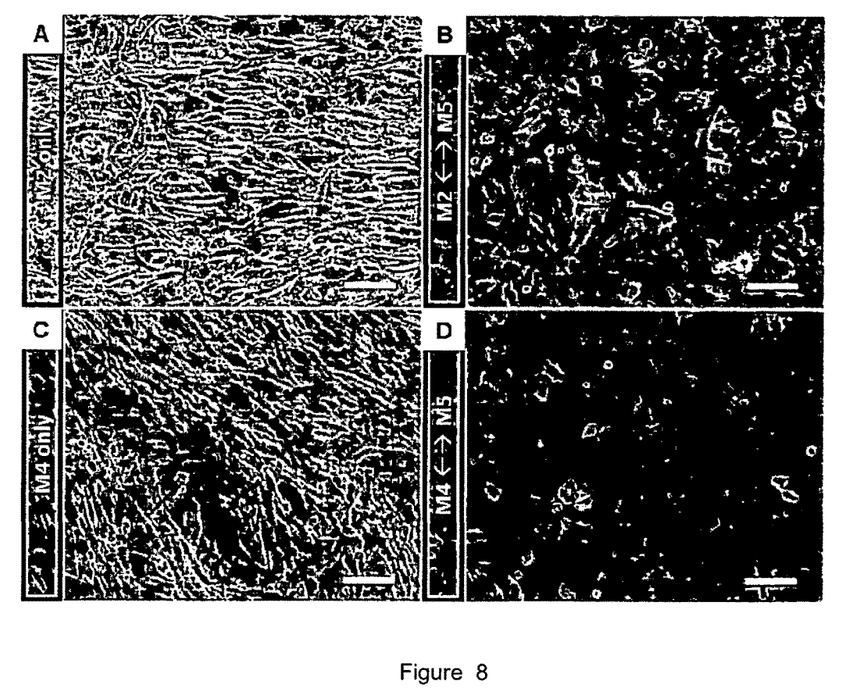
FIG. 8 Primary HCECs (P2, week 4) cultured in either (A) M2 only as compared to (B) M2 with exposure to M5, and (C) M4 only as compared to (D) M4 with exposure to M5 (Scale bar ~100 μm).

As mentioned, exposure of HCECs expanded in the proliferative media M2 or M4 to M5 significantly improved the morphology of HCECs. When cultured in either M2 or M4 only, isolated primary HCECs lose their unique polygonal morphology and turn fibroblastic. This form of transformation is rather unpredictable, but generally occurs from P3 onwards. In some cultures, signs of this occurrence of fibroblastic transformation in culture can be detected as earlier as P1. Interestingly, exposure to M5 in sets of HCECs that were expanded in either M2 or M4, significantly improved and preserved the unique morphology of HCECs (FIG. 8). In this aspect, it appeared that M5 acts as a maintenance medium that stabilized the cellular structure of HCECs. This has been consistent over various donor samples (FIG. 8).

Figure 9:
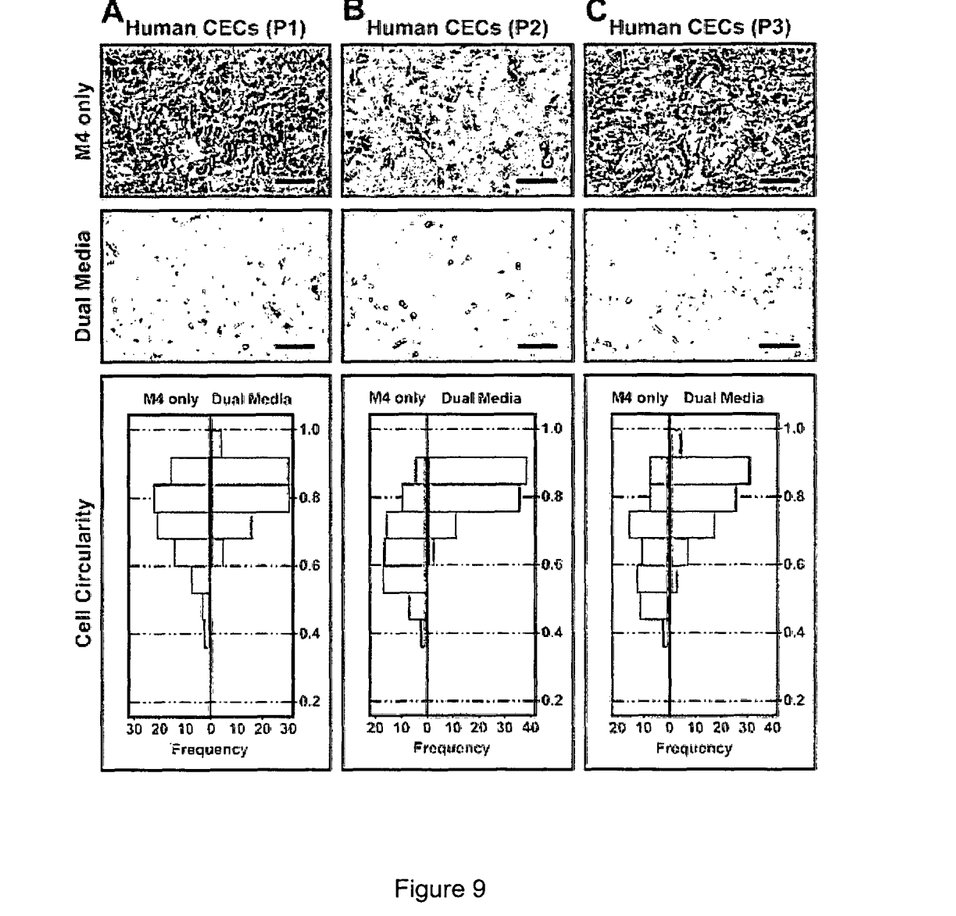
FIG. 9 Cellular morphology and circularity of human CECs cultured over three passages. Representative sets of photomicrographs showing morphology of confluent human CECs propagated in either M4 only as compared to cells propagated using the dual media approach, and a bar-chart comparing cell circularity for both conditions during (A): the first passage, (B): the second passage, and (C): the third passage.
Figure 10:
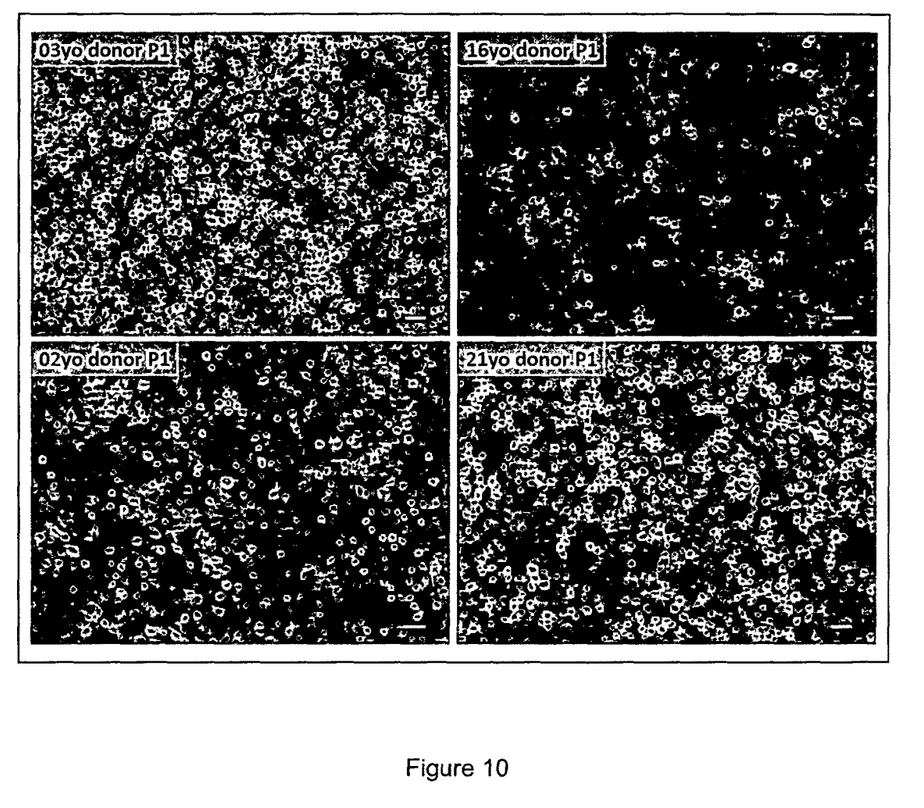
FIG. 10 Established HCECs from donors of varies ages using the Dual media approach at P1 (Scale bar ~100 μm).
Figure 11:
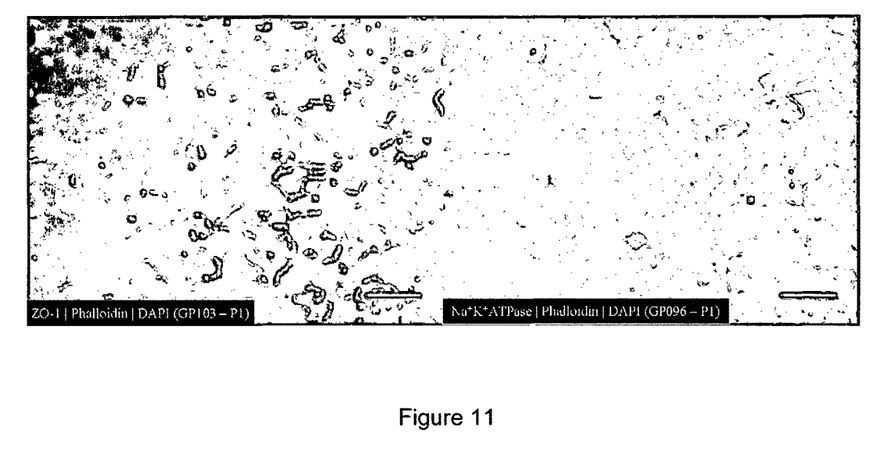
FIG. 11 Primary HCEC expanded in the dual media culture system express markers characteristic of human corneal endothelium ZO-1 and Na+Ka+ATPase (Scale bar ~100 μm).

As mentioned, exposure of HCECs expanded in the proliferative medium M4 to M5 significantly improved the morphology of HCECs. When cultured in M4 alone, isolated primary HCECs lose their unique polygonal morphology and turn fibroblastic. This phenomenon has been described as an endothelial-to-mesenchymal (EMT) transformation, resulting in an alternation of HCECs towards a more fibroblast-like morphology (Lee and Kay 2012). This form of transformation is rather unpredictable, but generally occurs from P2 onwards. In some cultures, signs of such occurrence can be detected as earlier as P1. Interestingly, exposure to M5 in sets of HCECs that were expanded in M4, significantly improved and preserved their unique cellular morphology as gauged by the cell circularity comparison between HCECs cultured in M4 only and those cultured using the dual media approach (FIG. 9). In this aspect, it appeared that M5 acts as a maintenance medium that stabilized the cellular structure of HCECs. This observation is consistent over several donor samples passage and using a seeding density of at least $1.0 \times 10^4$ cells per $cm^2$, the projected numbers of HCECs obtainable at the end of the third passage range from between $1.0 \times 10^7$ to $2.5 \times 10^7$ cells per pair of donor corneas (Table 3).

TABLE 3

Projection of the range of HCECs obtainable each passage at confluent.

| Passage No | Projected HCECs at each passage |
|---|---|
| P0 | $8.0 \times 10^5$ to $1.0 \times 10^6$ cells |
| P1 | $2.1 \times 10^6$ to $3.2 \times 10^6$ cells |
| P2 | $4.5 \times 10^6$ to $7.5 \times 10^6$ cells |
| P3 | $1.0 \times 10^7$ to $2.5 \times 10^7$ cells |

Based on the isolation protocol, the cultivation methodology described in this paper, and a seeding density of not less than $1.0 \times 10^4$ cells per $cm^2$, it is possible to scale up the number of HCECs to a range between $1.0 \times 10^7$ to $2.5 \times 10^7$ cells at confluence, bt the third passage from a pair of donor corneas.

Figure 7:
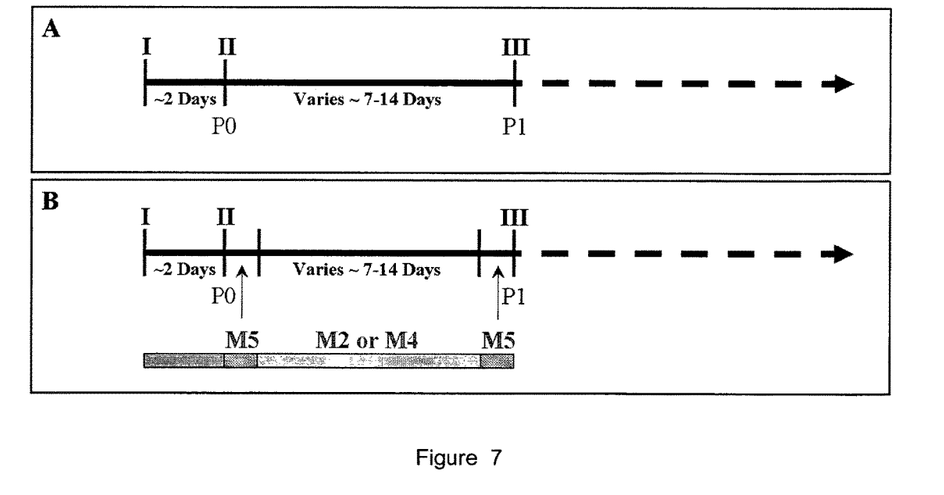

Primary HCECs expanded via the dual media culture system retained characteristic expression of ZO-1, a tight junction-associated protein, as well as Na+K+/ATPase which is associated to the fluid pump function of the corneal endothelium (FIG. 7). Functionality of HCECs is currently being assessed in a rabbit model of bulbous keratopathy. Further in vitro characterisation at the molecular level and in vivo validation of HCECs cultured using the dual media approach is currently underway.

Figure 12:
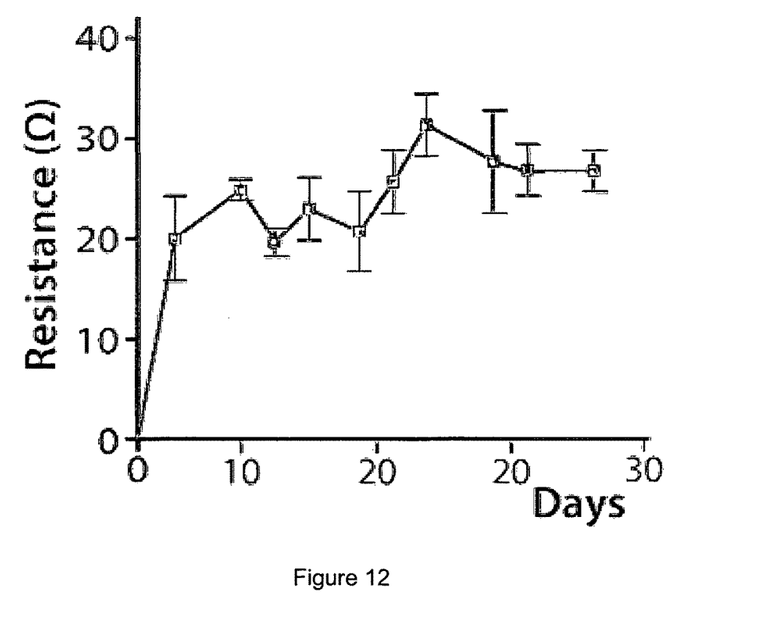
FIG. 12 Measurement of average resistance of cultivated P3 HCECs (n=3) after seeding. Resistance rapidly increases two days after seeding and slowly plateaus as an intact monolayer is formed.

The electrical resistance of cultivated HCECs (Passage 3) was measured using a hand-help epithelial/endothelial volt-ohm meter (EVOM). Cells were seeded at high density onto permeable 'Snapwell' support and resistance of the monolayer formed was measured for four weeks (FIG. 12). A plateau in the resistance levels was taken to indicate resistive stability and the formation of a complete and intact monolayer.

Figure 13:
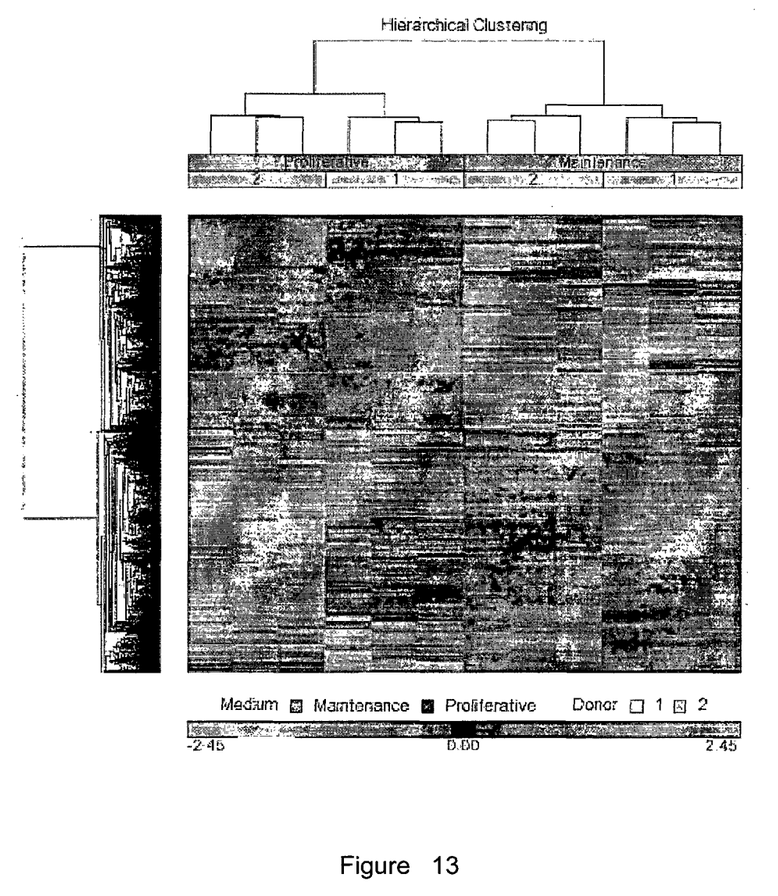
FIG. 13 Hierarchical clustering shows that the samples cluster according to the culture condition, indicating that HCECs cultured in M4 medium have more similar gene expression profiles compared to their counterparts after they were exposed and maintained in M5 medium.

As shown earlier (FIG. 9), the polygonal morphology of primary HCECs could be consistently maintained for each of the three rounds of expansion when the confluent cells grown in M4 were switched to M5. In order to better understand the observed morphological changes at the molecular level, high throughput microarray analysis was performed on human CECs isolated from two donor corneas and cultivated to the third passage. Here, global gene expression profile of the confluent human CECs expanded in M4 for the first and second donor, were compared to the same set of the confluent human CECs maintained in M5 medium for a further seven days. Hierarchical clustering showed that HCECs from the two donors cultured in M4 had more similarities in their gene expression profiles than cells from the same donors maintained in M5 for seven days more (FIG. 13). In all, we found a total of 1,485 genes that were up-regulated, and 1,420 genes down-regulated. Additionally, the top 10 up-regulated and down-regulated genes are listed in Table 4 and Table 5, respectively. Further analysis of the microarray data is currently underway and future in vivo validation of HCECs cultured using the dual media approach will be assessed in an animal model of bullous keratopathy.

TABLE 4

Top 10 up-regulated genes after exposure of human CECs to M5 medium

| Gene | Brief Description | GeneBank Accession No. |
|---|---|---|
| ANGPTL7 | Angiopoietin-like 7: modulates extracellular matrix deposition. | NM_021146.2 |
| H19 | H19: imprinted maternally expressed transcript. | NR_002196.1 |
| PTGDS | Prostaglandin D2 synthase 21 kDa: mediators of ultraviolet B light toxicity in cornea. | NM_000954.5 |
| SLC4A11 | Solute carrier family 4, sodium borate transporter, member 11: essential for cellular boron homeostasis, as well as cell growth and proliferation. | NM_032034.3 |
| ALPL | Alkaline phosphatase: membrane bound glycosylated enzyme. | NM_000261.1 |
| OLFML1 | Olfactomedin-like 1: secreted glycoprotein, regulation of cell proliferation in vitro. | NM_198474.3 |
| APLN | Apelin: involves in different tissue specific signaling pathways that regulate diverse biological functions including fluid homeostasis and insulin secretion | NM_000261.1 |
| ZP4 | Zona pellucida protein 4: glyocoprotein. | NM_021186.3 |
| MYOC | Myocilin: secreted glycoprotein: modulates organization of actin cytoskeleton, stimulating formation of stress fibers through Wnt signaling components. | NM_000261.1 |
| SFRP1 | Secreted frizzled-related protein 1: soluble modulator of Wnt signaling, and known to regulate cell growth and differentiation. | NM_003012.4 |

TABLE 5

Top 10 down-regulated genes after exposure of human CECs to M5 medium

| Gene | Brief Description | GeneBank Accession No. |
|---|---|---|
| LAMC2 | Laminin, gamma 2: major non-collagenous ECM glycoproteins constituent of basement membranes. | NM_005562.2 |
| ESM1 | Endothelial cell-specific molecule 1: secreted protein with a stipulated role in endothelium-dependent pathological disorder. | NM_007036.4 |
| GRP | Gastrin-releasing peptide: involved in smooth muscle cell contraction, and epithelial cell proliferation. | NM_002091.3 |
| RGS4 | Regulator of G-protein signaling 4: inhibits signal transduction by increasing the GTPase activity of G protein alpha subunits. | NM_001102445.2 |
| DKK1 | Dickkopf 1 homolog: secreted protein known to antagonize canonical Wnt signaling by inhibiting LRP5/6. | NM_012242.2 |
| LRRN3 | Leucine-rich repeat neuronal protein 3: a single-pass type I membrane protein containing 12 leucine-rich repeats. | NM_003641.3 |
| VCAN | Versican: Chondroitin sulfate proteoglycan, a major component of the extracellular matrix | NM_005556.3 |
| MFAP5 | microfibrillar associated protein 5: a 25-kD microfibril-associated glycoprotein rich in serine and threonine residues. Component of the elastin-associated microfibrils | NM_001102445.2 |
| ISG15 | ISG15 ubiquitin-like modifier: a ubiquitin-like protein conjugated to many cellular proteins upon activation by interferon-alpha | NM_005101.3 |
| DDIT4L | DNA-damage-inducible transcript 4-like: mediates cell growth by regulation of TOR signaling pathway. | NM_145244.3 |

REFERENCES

Amano S (2003) Transplantation of cultured human corneal endothelial cells Cornea 22(7 Suppl):S66-574

Blake Da, Yu H, Young D L and Caldwell D R (1997); Matrix stimulates the proliferation of human corneal endothelial cells in culture; Invest Ophthalmol Vis Sci 38(6):1119-29

Engelmann K and Friedl P (1989) Optimization of culture conditions for human corneal endothelial cells; In Vitro Cell Dev Biol 25(11):1065-72

Engelmann K and Fried P (1995) Growth of human corneal endothelial cells in a serum-reduced medium; 14(1):62-70

Green and Sambrook (2012) Molecular Cloning: A Laboratory Manual, Cold Springs Harbor Laboratory, New York Ishino Y, Sano Y, Nakamura T, Connon C J, Rigby H, Fullwood N J and Kinoshita S (2004) Amniotic membrane as a carrier for cultivated human corneal endothelial cell transplantation; Invest Ophthalmol Vis Sci 45(3): 800-6

Lee J G and Kay E P (2012) NF-κB is the transcription factor for FGC-2 that causes endothelial mesenchymal transformation in cornea; Invest Ophthalmol Vis Sci 53(3):1530-8

Li W, Sabatar A L, Chen Y T, Hayashida Y, Chen S Y, He H and Tseng S C (2007) A novel method of isolation, preservation and expansion of human corneal endothelial cells; Invest Ophthalmol Vis Sci 48(2):614-620

Miyata I, Drake J, Osakabe Y, Hosokawa Y, Hwang D, Soya K, Oshika T and Amano S (2001) Effect of donor age on morphologic variation of cultured human corneal endothelial cells; Cornea 20(1):59-63

Pistsov M Y, Sadovnikova Eyu and Danilov S M (1988); Human corneal endothelial cells: isolation, characterization and long-term cultivation; Exp Eye Res 47(3):403-414

Yue B Y, Sugar J, Gilboy J E and Elvart J L (1989); Growth of human corneal endothelial cells in culture; Invest Ophthalmol Vis Sci 30(2):248-253

Zhu C and Joyce N C (2004) Proliferative response of corneal endothelial cells from young and older donors Invest Opthamol Vis Sci 45(6):1743-51

The invention claimed is:

1. A method for culturing isolated corneal endothelial cells comprising the steps of:

(i) contacting isolated primary corneal endothelial cells with a maintenance medium comprising Human Endothelial-Serum Free Medium (Human Endothelial-SFM) to stabilize the corneal endothelial cells (ii) contacting the isolated stabilized corneal endothelial cells with a proliferative medium to propagate and/or expand the corneal endothelial cells; and (iii) contacting the propagated and/or expanded corneal endothelial cells with the maintenance medium comprising Human Endothelial-SFM to substantially preserve the morphology and characteristics of the corneal endothelial cells.

2. The method according to claim 1, wherein step (ii) comprises culturing the isolated corneal endothelial cells in the proliferative medium.

3. The method according to claim 1, wherein step (iii) is performed before the isolated corneal endothelial cells differentiate or change morphology and/or characteristics.

4. The method according to claim 1 wherein step (iii) comprises replacing the proliferative medium with the maintenance medium.

5. The method according to claim 1, wherein step (iii) comprises passaging the propagated and/or expanded corneal endothelial cells in the maintenance medium.

6. The method according to claim 1, wherein the proliferative medium comprises a supplemented basal medium.

7. The method according to claim 6, wherein the proliferative medium comprises a basal medium supplemented with at least one supplement selected from the group consisting of amino acids, antimicrobials, cholera toxin, chondroitin, Dimethyl sulphoxide (DMSO), Endothelial Cell Growth Supplement (ECGS), growth factors, insulin, steroids, minerals, pituitary extract, transferrin and vitamins.

8. The method according to claim 1, wherein the proliferative medium comprises a basal medium supplemented with serum.

9. The method according to claim 1, wherein the proliferative medium comprises a basal medium supplemented with at least 2% serum.

10. The method according claim 1, wherein the proliferative medium comprises a basal medium supplemented with 5% serum.

11. The method according to claim 1, wherein the maintenance medium comprises Human Endothelial-SFM supplemented with serum.

12. The method according to claim 11, wherein the maintenance medium comprises Human Endothelial-SFM supplemented with at least 2% serum.

13. The method according to claim 11 or 12, wherein the maintenance medium comprises Human Endothelial-SFM supplemented with 2.5% or 5% serum.

14. The method according to claim 1, wherein the maintenance medium comprises Human Endothelial-SFM supplemented with at least one antimicrobial.

15. The method according to claim 1, wherein the proliferative medium comprises M2 or M4 medium.

* * * * *